(12) United States Patent
Norris et al.

(10) Patent No.: US 6,823,213 B1
(45) Date of Patent: Nov. 23, 2004

(54) IMPLANTABLE MEDICAL DEVICE AND METHOD USING INTEGRATED T-WAVE ALTERNANS ANALYZER

(75) Inventors: John F. Norris, Largo, FL (US); Geeske Van Oort, Nieuwleusen (NL); Dave J. Munneke, Arnhem (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/558,871

(22) Filed: Apr. 28, 2000

(51) Int. Cl.[7] ............................................... A61N 1/362
(52) U.S. Cl. .................................... 607/9; 600/516
(58) Field of Search ................................ 600/508–509, 600/515–518; 607/4–5, 9, 14, 17, 25, 26

(56) References Cited

U.S. PATENT DOCUMENTS

| | | | | |
|---|---|---|---|---|
| 5,271,393 A | * | 12/1993 | Callaghan | 607/14 |
| 5,497,780 A | * | 3/1996 | Zehender | 600/374 |
| 5,827,195 A | * | 10/1998 | Lander | 600/509 |
| 5,842,997 A | * | 12/1998 | Verrier et al. | 600/518 |
| 6,058,328 A | * | 5/2000 | Levine et al. | 607/14 |
| 6,148,230 A | * | 11/2000 | KenKnight | 600/516 |
| 6,169,919 B1 | * | 1/2001 | Nearing et al. | 600/518 |

* cited by examiner

*Primary Examiner*—Kennedy Schaetzle
*Assistant Examiner*—Kristen Droesch
(74) *Attorney, Agent, or Firm*—Daniel G. Chapik; Girma Wolde-Michael

(57) ABSTRACT

An implantable medical device includes a sensor and a T-wave analyzer. The sensor is implantable within the body of a patient to sense electrical cardiac activity and provide an indication of T-wave alternans within the heart of the patient. The T-wave analyzer is responsive to the sensor, and evaluates cardiac risk based on comparison of the indication of T-wave alternans to a predetermined criterion. The T-wave analyzer may form part of a microprocessor, a digital signal processor, or combination of both. The device may include a pacing generator that applies increased rate pacing stimuli to the heart to facilitate sensing of the T-wave alternans by the sensor. The device also may incorporate a memory that stores the T-wave alternans indication provided by the sensor, e.g., over a number of heartbeats. In addition, the device may be equipped to provide an alert to the patient or a physician in the event the processor generates the indication of cardiac risk. The results of the T-wave alternans analysis over a period of time can be stored as data in memory for access by a physician, e.g., by telemetry. In response to the alternans data, the physician may prescribe pharmacologic therapy, programmed cardiac electrical stimulation, or modifications to an electrical stimulation program in the existing implanted device. In some cases, the implantable medical device can be programmed to response to the alternans data, e.g., by controlling a pacing generator.

43 Claims, 9 Drawing Sheets

IMPLANTABLE MEDICAL DEVICE AND METHOD USING INTEGRATED T-WAVE ALTERNANS ANALYZER

FIELD OF THE INVENTION

This invention relates generally to the field of cardiology and, more particularly, to analysis of cardiac electrical activity for identification and therapy of patients at risk for sudden cardiac death.

BACKGROUND OF THE INVENTION

Analysis of cardiac electrical activity can provide significant insight into the risk state of a patient for sudden cardiac death, and is the major objective in the science of cardiology. Identification of spurious electrical activity within the heart can provide the physician with clues as to the relative cardiac risk presented to the patient. Equipped with such clues, the physician is better able to prescribe therapy for the patient. If a patient is at significant risk, for example, the physician may prescribe pharmacologic therapy, programmed cardiac electrical stimulation, e.g., via an implanted pacemaker or defibrillator, or modifications to the electrical stimulation program in an existing implanted device.

Analysis of T-wave alternans is one mode for identification of sudden cardiac death risk. For purposes of this description, the term "T-wave" may refer to a portion of an electrocardiogram that includes the T-wave and the ST segment. T-wave alternans refers to an alternation in the morphology of the T-wave in an AB-AB pattern. In particular, different rates of repolarization of the muscle cells in the ventricles in an alternating pattern have been associated with a variety of clinical conditions including prolonged QT syndrome, acute myocardial ischemia, and elecrolyte disturbance. Nonuniform repolarization can cause electrical instability in the heart. Indeed, T-wave alternans has been recognized as a significant indicator of risk for ventricular arrhythmia and sudden death.

Visual analysis of T-wave alternans using an electrocardiogram ordinarily is impractical due to the minute differences in signal amplitude. At the same time, however, T-wave alternans at even the microvolt level has been identified as an indicator of electrically unstable myocardium. For this reason, computer-based morphology analysis, as well as comparisons in the time and frequency domain, have been used for T-wave analysis. Recently, studies have demonstrated that T-wave alternans, measured upon induction of an elevated heart rate in the patient, is highly predictive of subsequent ventricular tachyarrhythmias and sudden death in patients with a variety of clinical conditions. Such studies typically make use of noninvasive ECG techniques relying on special electrodes that promote noise suppression.

A number of prior art disclosures have been made suggesting techniques for analysis of the T-wave to quantify T-wave alternans, including:

TABLE 1

| Country | U.S. Pat. No. | Inventor/Applicant | Issue Date |
|---|---|---|---|
| U.S.A. | 5,560,368 | Berger | 1996 |
| U.S.A. | 5,560,370 | Verrier et al. | 1996 |
| U.S.A. | 5,921,940 | Verrier et al. | 1999 |
| U.S.A. | 5,935,082 | Albrecht et al. | 1999 |

TABLE 1-continued

All patents listed in Table 1 above are hereby incorporated by reference herein in their respective entireties. As those of ordinary skill in the art will appreciate readily upon reading the Summary of the Invention, Detailed Description and Claims set forth below, many of the devices and methods disclosed in the patents of Table 1 may be modified advantageously by using the teachings of the present invention.

SUMMARY OF THE INVENTION

It is an object of this invention to provide an implantable medical device with an integrated T-wave alternans analyzer for cardiac risk evaluation. It is another object of the invention to provide an implantable medical device that facilitates T-wave alternans analysis without the external equipment such as surface electrodes ordinarily required and, in some cases, without immediate medical supervision. Along those lines, it is a further object to enable T-wave alternans analysis on a more frequent and convenient basis to thereby increase the likelihood of detecting cardiac risks associated with T-wave alternans.

In accordance with the above objectives, a T-wave alternans analyzer may be integrated, for example, with an implantable pacemaker or cardioverter/defibrillator. Integration of the T-wave alternans analyzer with other implantable medical devices such as heart pumps, cardiomyostimulators, ischemia treatment devices, drug delivery devices, and the like also is envisioned. In each case, the T-wave alternans analyzer may be capable of indicating whether the patient is at risk for sudden cardiac death or dangerous ventricular arrhythmias.

In some embodiments, there is provided an implantable medical device having a sensor and a T-wave analyzer. The sensor is implantable within the body of a patient to sense electrical cardiac activity and provide an indication of T-wave alternans within the heart of the patient. The T-wave analyzer is responsive to the sensor, and evaluates cardiac risk based on comparison of T-wave alternans to a predetermined criterion.

In a preferred embodiment, the T-wave analyzer may form part of a microprocessor, a digital signal processor (DSP), or a combination of both. Thus, T-wave sensing can be achieved by conventional analog sense circuitry or the more recently introduced DSP technology. In particular, the device may incorporate analog sense circuitry that processes the analog T-wave signal, or a digital signal processor that performs a similar operation with respect to the digitized T-wave signal, as desired. Digital signal processors have advanced to the degree that cardiac signals may be digitized and analyzed in real time. T-wave signal analysis and comparison to applicable criteria may take place within the DSP or analog circuitry, as well as within processor circuitry resident within the implantable medical device. The T-wave analyzer may be dedicated to T-wave alternans analysis or adapted to perform that function.

The device may include a pacing generator that applies increased rate pacing stimuli to the heart to facilitate sensing of the T-wave alternans by the sensor. In some embodiments, however, it is desirable that the device monitor T-wave alternans on a periodic or triggered basis including times at which the increased rate pacing stimuli has not been applied. For example, the patient may be subjected to exertion or stress in the ordinary course of his daily routine. At such times, it may be desirable to measure T-wave alternans even though the patient has not been affirmatively forced into the measurement mode, e.g., by increased rate pacing. Monitoring of stress and exertion using activity sensors, analysis of heart rate, and the like may provide a trigger for the T-wave alternans analysis.

The device also may incorporate a memory that stores the T-wave alternans indication provided by the sensor, e.g., over a number of heartbeats. The physician may interrogate the memory for more detailed analysis of the T-wave alternans data at a later time. In addition, the device may be equipped to provide an alert to the patient or a physician in the event the processor generates the indication of cardiac risk.

The T-wave analyzer, in some embodiments, may apply known signal processing techniques to quantify and detect T-wave alternans. For example, the T-wave analyzer may analyze T-wave alternans by reference to portions of the electrocardiogram incorporating the T-wave and other components. The T-wave alternans analysis may rely, in some embodiments, on energy, amplitude, magnitude, time and slope differences in the QT interval. The interval can be monitored over a series of two or more alternating heartbeats, for example, to evaluate the cardiac risk.

In addition, the T-wave analyzer may apply a Fourier analysis to the T-wave, and provide the indication of T-wave alternans based on differences in the Fourier analysis over a series of two or more heartbeats. Fourier analysis can be effective in revealing beat-to-beat differences. In some embodiments, the T-wave analyzer can be configured to count the number of times the T-wave alternans satisfies an alternans criterion, and generate an indication of cardiac risk in the event the number exceeds a predetermined threshold.

The results of the T-wave alternans analysis over a period of time can be stored as data in memory for interrogation by a physician, e.g., by telemetry. In response to the alternans data, the physician may prescribe pharmacologic therapy, programmed cardiac electrical stimulation, or modifications to an electrical stimulation program in an existing implanted device.

In some cases, the implantable medical device can be programmed to proactively respond to the alternans data, e.g., by activating an alert for the patient or a physician, modulating a pacing generator, dispensing a drug or other substance from an implanted pump. In this manner, the physician, the implanted device, or both can take action in response to acute and long-term risks indicated by the T-wave alternans analysis.

Various embodiments of the invention are set forth in the accompanying drawings and the description below. Other features and advantages of the invention will become apparent from the description, the drawings, and the claims.

DETAILED DESCRIPTION OF THE PREFERRED EMBODIMENTS

Figure 1:
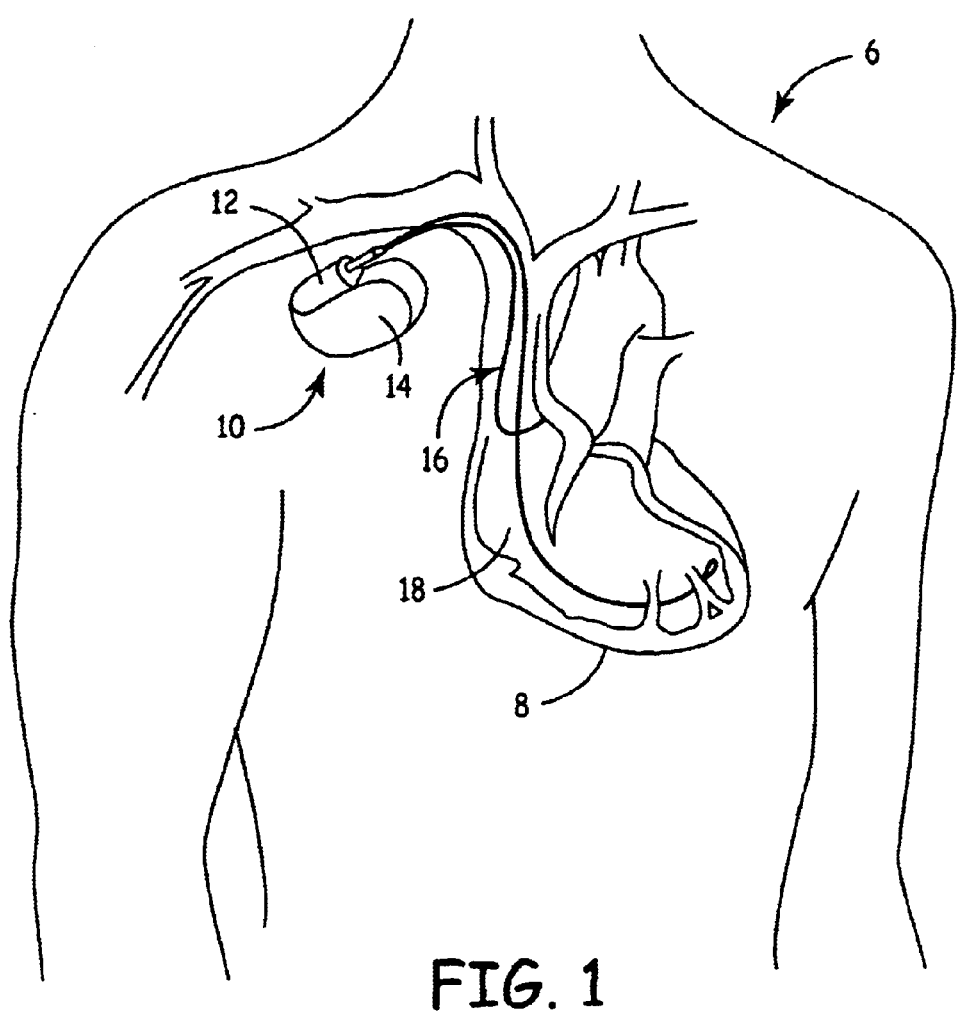
FIG. 1 illustrates an implantable medical device system in accordance with an embodiment of the invention implanted in a human body.

FIG. 1 is a simplified schematic view of one embodiment of implantable medical device ("IMD") 10 of the present invention implanted within a human body 6. As will be described, IMD 10 may be equipped with an integrated T-wave alternans analyzer to enable assessment of the risk of sudden cardiac death. IMD 10 comprises hermetically sealed enclosure 14 and connector module 12 for coupling IMD 10 to pacing and sensing leads 16 and 18 that are implanted near heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all hereby incorporated by reference herein, each in its respective entirety. A variety of pacemakers suitable for incorporation of a T-wave alternans analyzer are commercially available from Medtronic of Minneapolis, Minn. and Medtronic subsidiary Vitatron, Inc.

Figure 2:
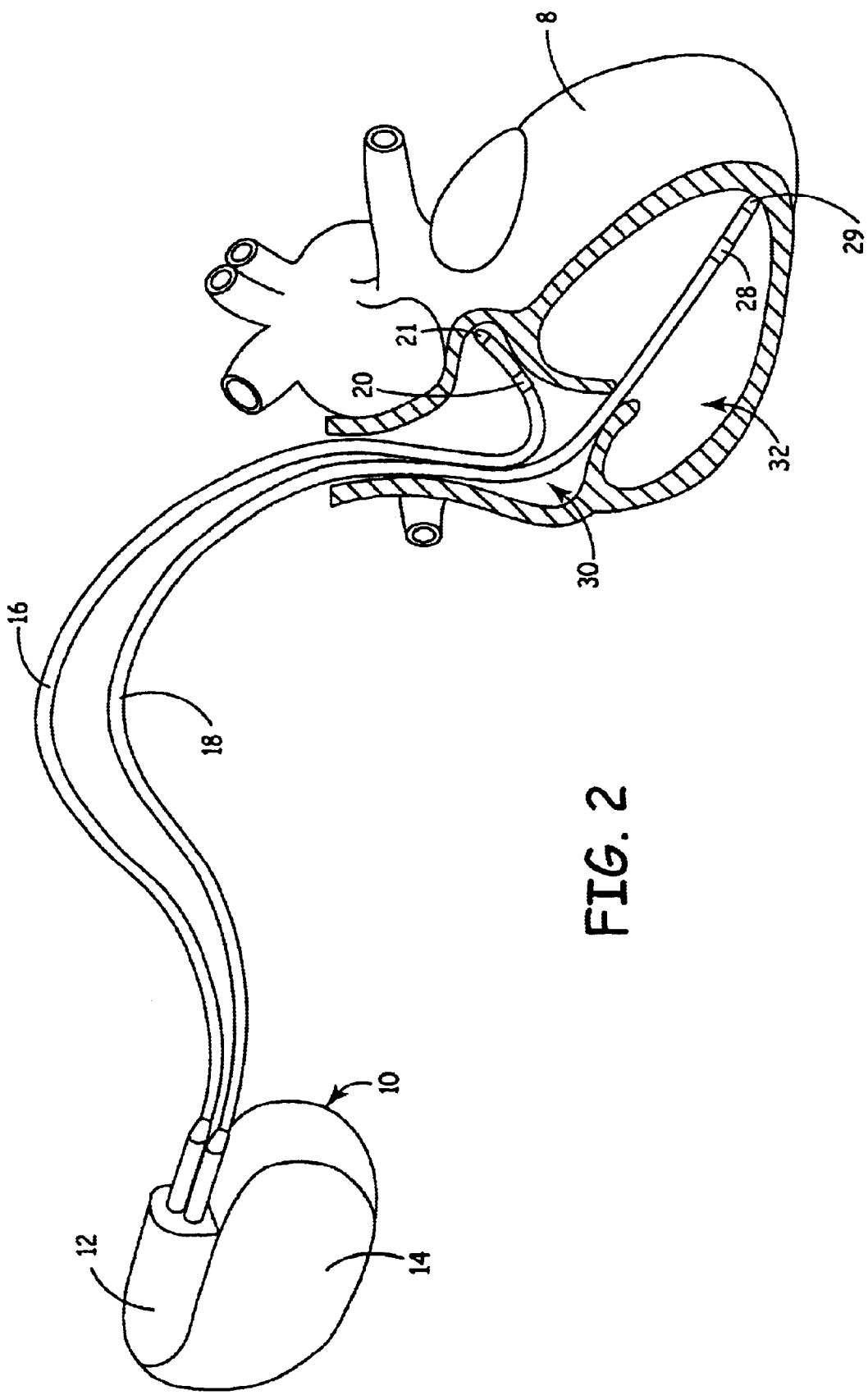
FIG. 2 illustrates one embodiment of an implantable pacemaker device system in accordance with the present invention coupled to a human heart.

FIG. 2 shows connector module 12 and hermetically sealed enclosure 14 of IMD 10 located in and near heart 8. Atrial and ventricular pacing leads 16 and 18 extend from connector module 12 to the right atrium 30 and ventricle 32, respectively, of heart 8. Atrial electrodes 20 and 21 disposed at the distal end of atrial pacing lead 16 are located in the right atrium 30. Ventricular electrodes 28 and 29 at the distal end of ventricular pacing lead 18 are located in the right ventricle 32.

Figure 3:
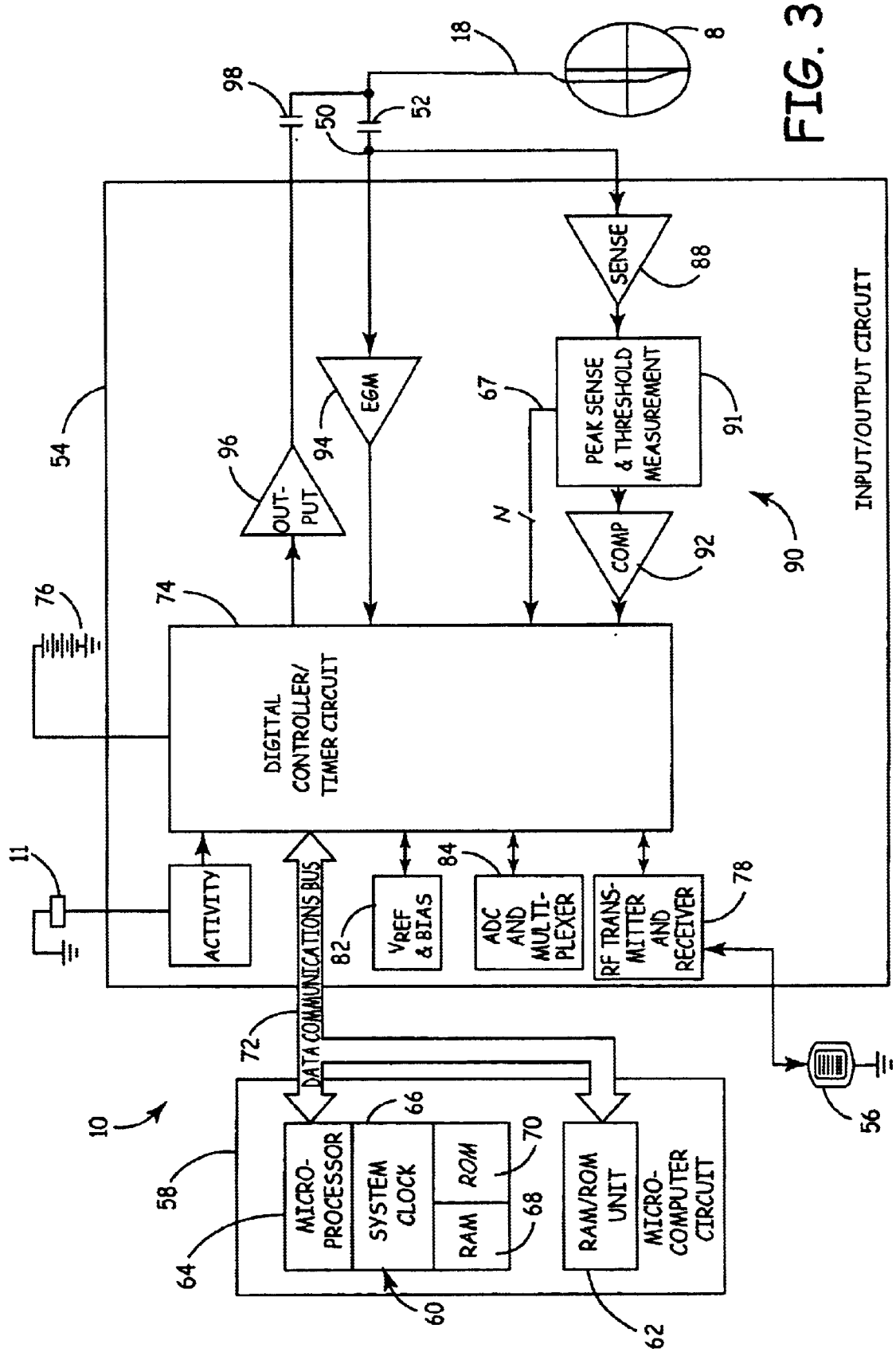
FIG. 3 is a block diagram illustrating the various components of one embodiment of an implantable pacemaker device configured to operate in accordance with the present invention.

FIG. 3 shows a block diagram illustrating the constituent components of IMD 10 in accordance with one embodiment of the present invention, where IMD 10 is pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown in the figures). One such programmer is the commercially available Medtronic/Vitatron Model 9790 programmer, which is microprocessor-based and provides a series of encoded signals to IMD 10, typically through a programming head that transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored in microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

As further shown in FIG. 3, VREF and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data bus 72 to digital controller/timer circuit 74, where digital timers and counters establish an overall escape interval of the IMD 10 as well as various refractory, blanking and other timing windows for controlling the operation of peripheral components disposed within input/output circuit 54.

Digital controller/timer circuit 74 is preferably coupled to sensing circuitry 91, including sense amplifier 88, peak sense and threshold measurement unit 90 and comparator/threshold detector 92. The embodiment of FIG. 4 conforms substantially to that shown in FIG. 3; but incorporates a digital signal processor (DSP) 101 in lieu of sensing circuitry 90, including sense amplifier 88, peak sense and threshold measurement unit 91, and comparator/threshold detector 92. DSP 101 receives signals, which may be amplified and processed, from lead 18. DSP 101 digitizes the signals for analysis. DSP 101 may be coupled to micro-computer circuit 58 via data communications bus 72, permitting the micro-computer circuit to modify the processing characteristics of the DSP. Also, DSP101 may provide signal data to micro-computer circuit 58 for added analysis or control functions. An example of an implantable medical device incorporating a DSP for ECG signal analysis is disclosed in U.S. Pat. No. 6,029,087 to Wohlgemuth, the entire content of which is incorporate herein by reference.

Digital controller/timer circuit 74 is further preferably coupled to electrogram (EGM) amplifier 94 for receiving amplified and processed signals sensed by lead 18. In the embodiment of FIG. 3, sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. Alternatively, similar signals can be generated by DSP 101 for transmission to digital controller/timer circuit 74. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8. In some preferred embodiments of the present invention, IMD 10 may operate in various non-rate-responsive modes, including, but not limited to, DDD, DDI, VVI, VOO and VVT modes.

In other preferred embodiments of the present invention, IMD 10 may operate in various rate-responsive modes, including, but not limited to, DDDR, DDIR, VVIR, VOOR and VVTR modes. Some embodiments of the present invention are capable of operating in both non-rate-responsive and rate responsive modes. Moreover, in various embodiments of the present invention, IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single, dual-, triple- or quadruple-chamber pacemakers or other types of IMD's. See, for example, U.S. Pat. No. 5,800,465 to Thompson et al., hereby incorporated by reference herein in its entirety, as are all U.S. Patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all hereby incorporated by reference herein, each in its respective entirety.

Figure 4:
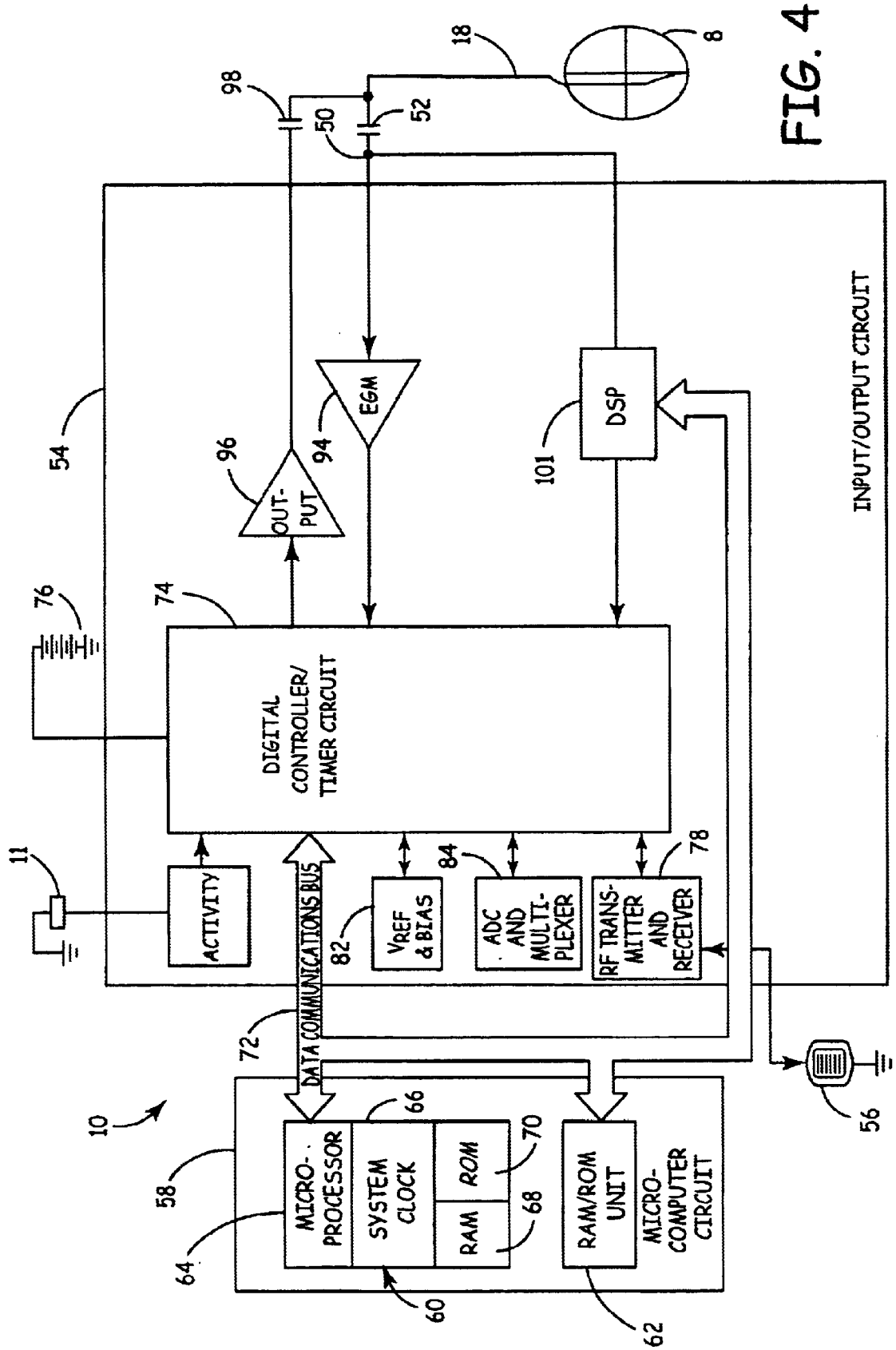
FIG. 4 is a block diagram illustrating the various components of another embodiment of an implantable pacemaker device configured to operate in accordance with the present invention.
Figure 5:
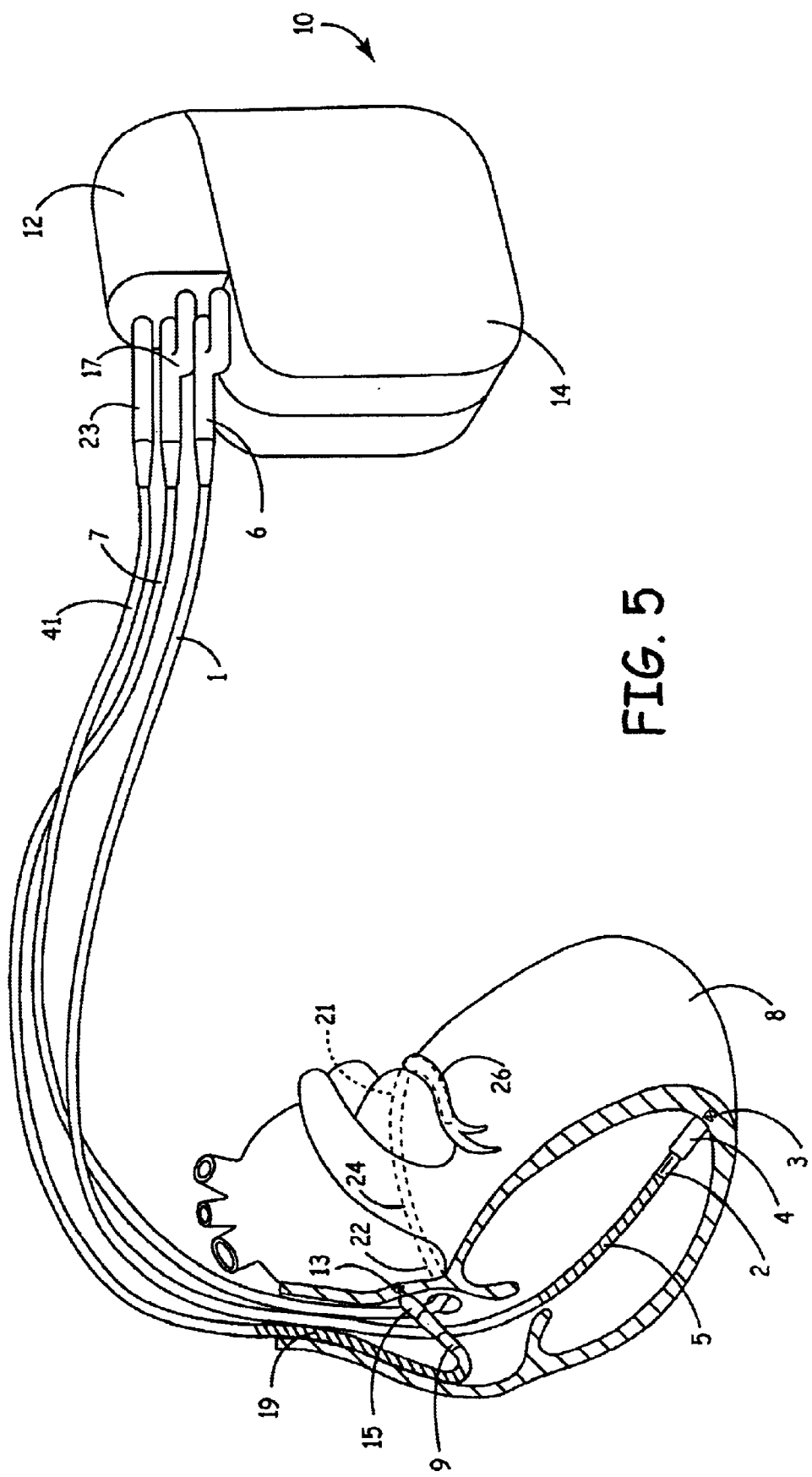
FIG. 5 illustrates one embodiment of an implantable pacemaker cardioverter defibrillator in accordance with the present invention coupled to a human heart.

FIGS. 3–5 illustrate embodiments in which IMD 10 is a PCD. In FIG. 5, the ventricular lead can take the form of leads disclosed in U.S. Pat. Nos. 5,099,838 and 5,314,430 to Bardy, and includes an elongated insulative lead body 1 carrying three concentric coiled conductors separated from one another by tubular insulative sheaths.

Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6 which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 5 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead 41 shown in FIG. 5 is located within the coronary sinus and great vein of heart 8. Pacing lead 41 is inserted such that a blood flow velocity sensor 22 within pacing electrode 41 produces a signal representing the flow rate of blood through the coronary sinus. In one configuration, as discussed in detail below, coronary sinus lead 41 can be a unipole or dipole pacing lead for delivering prophylactic arrhythmia therapy when a cardiac event, such as a myocardial infarction, is detected. At the proximal end of lead 41 is connector plug 23 carrying an electrical connector coupled to the coiled conductor. The coronary sinus pacing lead 41 may be about 5 cm in length.

Implantable PCD 10 is shown in FIG. 5 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 5 may be practiced in conjunction with the present invention, such as those shown in U.S. Pat. No. 5,690,686 to Min et al., hereby incorporated by reference herein in its entirety.

Figure 6:
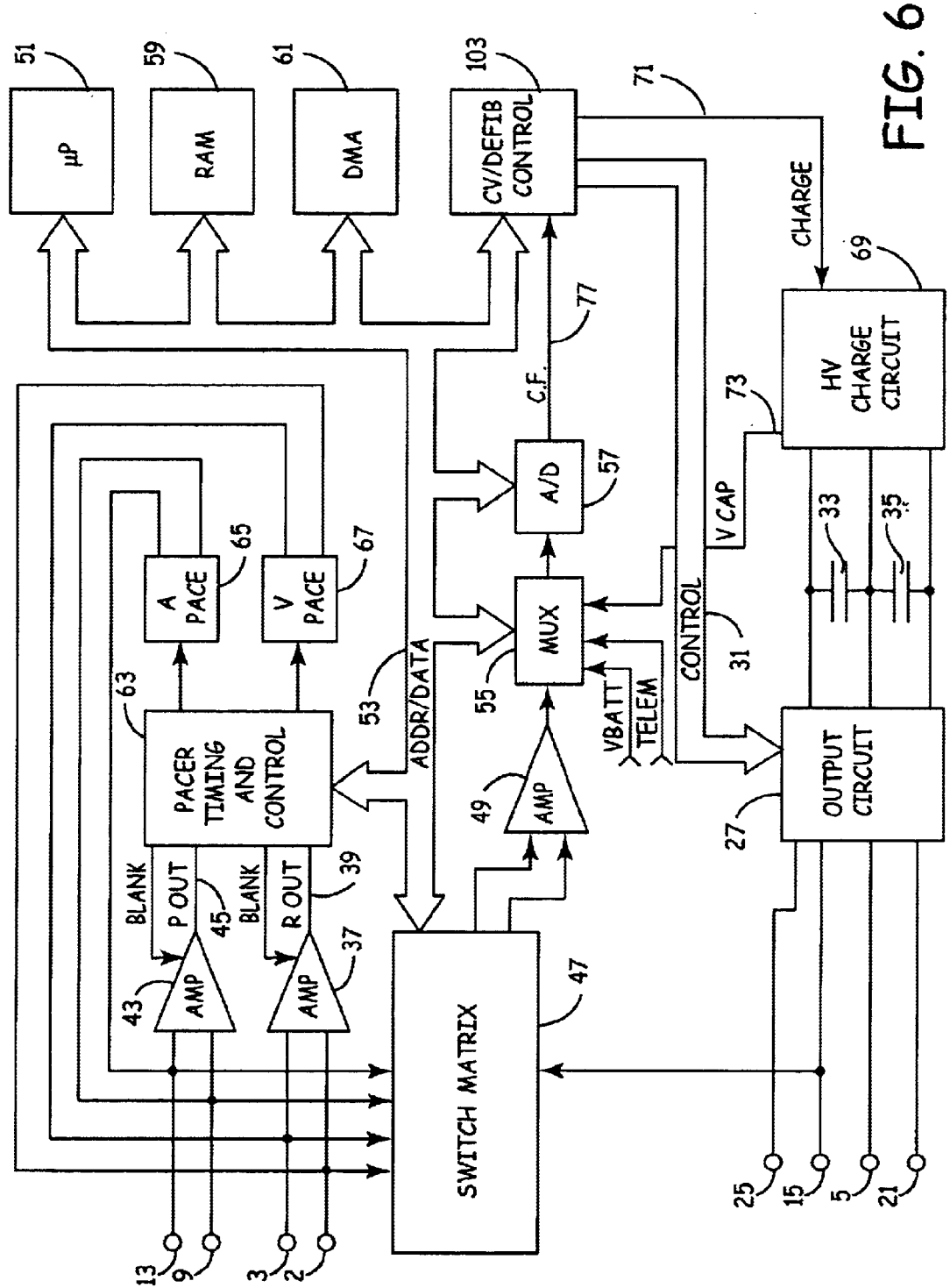
FIG. 6 is a block diagram illustrating the various components of one embodiment of an implantable pacemaker cardioverter defibrillator configured to operate in accordance with the present invention.

FIG. 6 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 5 is employed, the correspondence to the illustrated electrodes is as follows. Electrode 25 in FIG. 6 includes the uninsulated portion of the housing of PCD 10. Electrodes 25, 15, 21 and 5 are coupled to high voltage output circuit 27, which includes high voltage switches controlled by CV/defib control logic 103 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals,"hereby incorporated by reference herein in its entirety.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by AND converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular (AV) pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R-R intervals, P-P intervals, P-R intervals and R-P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al. and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser. No. US92/02829, Publication No. W092/18198, by Adams et al., and in the article "Automatic Tachycardia Recognition", by Arzbaecher et al., published in PACE, May-June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 103, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Delivery of cardioversion or defibrillation pulses is accomplished by output circuit 27 under the control of control circuitry 103 via control bus 31. Output circuit 27 determines whether a monophasic or biphasic pulse is delivered, the polarity of the electrodes and which electrodes are involved in delivery of the pulse. Output circuit 27 also includes high voltage switches that control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Figure 7:
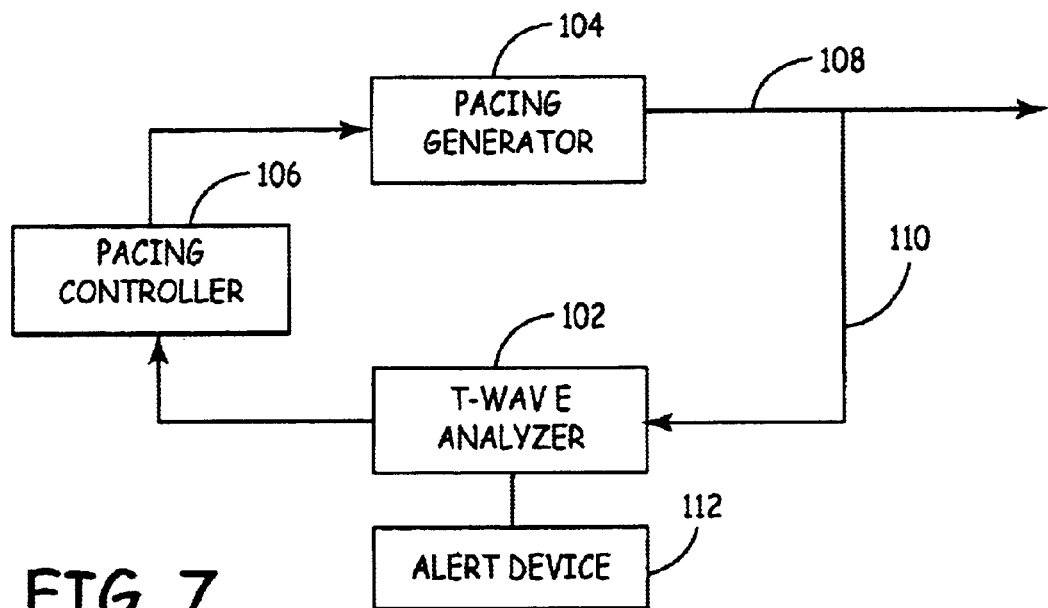
FIG. 7 is a block diagram illustrating an implantable medical device system incorporating a T-wave alternans analyzer in accordance with the present invention.

FIG. 7 is a block diagram illustrating the functional components of an implantable medical device system incorporating a T-wave alternans analyzer in accordance with the present invention. As shown in FIG. 7, the system may include a T-wave analyzer 102, a pacing generator 104, a pacing controller 106, pacing lead 108, connecting line 110, and alert device 112. The embodiment of FIG. 7 is intended to represent the primary functional components adapted for use in T-wave analysis from an implantable medical device system as shown in any of FIGS. 3, 4, or 6. T-wave analyzer 102, for example, may take the form of DSP 101 or analog sense circuitry (88, 91, 92) as shown in FIGS. 3 and 4, in combination with programmed logic resident in digital controller/timer circuit 74, or microprocessor 64 in the embodiments of FIGS. 3 and 4. Alternatively, in the embodiment of FIG. 6, T-wave analyzer 102 may take the form of a DSP or analog sense circuitry in combination with programmed logic resident in pacer timing and control circuit 63 or microprocessor 51. Similarly, pacing controller 106 may take the form of programmed logic within the microprocessors or control circuitry of the embodiments of FIGS. 3, 4, and 6, while pacing generator 104 may be realized by adaptation of digital controller timer circuit 74 in FIGS. 3 and 4 or pacer timing control circuit 63 in FIG. 6. In addition, lead 108 can be realized by a lead 18 as shown in FIGS. 3 and 4 and may include one, two or more leads.

In the system shown in FIG. 7, pacing controller 106 controls pacing generator 104 to apply a predetermined electrical pacing stimulus to the heart via lead 108. T-wave analyzer 102 senses the ECG signal generated by the heart via lead 108 and connecting line 110. In this manner, lead 108 functions as an implanted sensor for T-wave analysis. T-wave analyzer 102 can be configured to sense a variety of electrical characteristics indicative of T-wave alternans by processing signals received on alternating beats of the heart. Pacing controller 106 can be made responsive to T-wave analyzer 102 in two ways. First, to facilitate sensing and quantification of T-wave alternans, pacing controller 106 preferably is responsive to the initiation of sensing by T-wave analyzer 102 by controlling pacing generator 104 to apply electrical pacing stimuli with an increased pacing rate. In this manner, the desired physiological conditions for T-wave alternans analysis can be invoked internally by the implantable medical device itself. As a result, T-wave alternans analysis can take place virtually anywhere and at any time without the need for direct supervision by the physician. As an alternative, the patient may be asked by a physician to engage in semi-vigorous exercise to achieve the desired condition.

Second, pacing controller 106 may be made responsive in the event significant T-wave alternans is detected by T-wave analyzer 102, e.g., by comparison of the quantified alternans to a predetermined criterion, such as a threshold. In this case, pacing controller 106 may be programmed to execute a therapeutic pacing program designed to treat the heart in the event T-wave alternans is significantly elevated. In other embodiments, T-wave analyzer 102 may be coupled to or form part of other implantable medical devices, such as heart pumps, cardiomyostimulators, ischemia treatment devices, drug delivery devices, and the like. In such cases, the alternative device may be configured to respond to the indication of significant T-wave alternans by delivery of other forms of therapy. An implanted drug delivery device, for example, could be configured to deliver drugs or gene therapy to the heart to treat the condition in indicated by T-wave analyzer 102.

T-wave analyzer 102 also may be configured to activate an alert device 112 within the implanted device. Alert device 112 may provide alerts in a variety of ways. For example, in the event significant T-wave alternans is indicated, the alert may take one or more of the following forms: (a) alert a patient and/or physician audibly or otherwise of the patient's detected condition; (b) telemetrically communicate the patient's change in condition to a nearby external communication device, programmer or computer, which may then be further pre-programmed to telephonically, by internet, or otherwise alert a hospital, physician or emergency medical service of the patient's detected condition; (c) provide an appropriate cardiac pacing therapy such as anti-tachycardia pacing to treat the condition; (d) provide an appropriate cardiac defibrillation therapy to treat the condition; (e) provide an appropriate cardioversion therapy to treat the condition; (e) dispense a predetermined amount of a drug or gene therapy into the patient's bloodstream or cardiac tissue, as mentioned above, by means of an implantable drug pump forming a part of, attached to or in communication with the pacing or defibrillation device or its associated electrical stimulation and/or sensing leads; or (f) capture detailed diagnostic data over a predetermined time period for subsequent processing and analysis by a physician. Alert device 112 may be adapted from components present in the implantable medical device.

Figure 8:
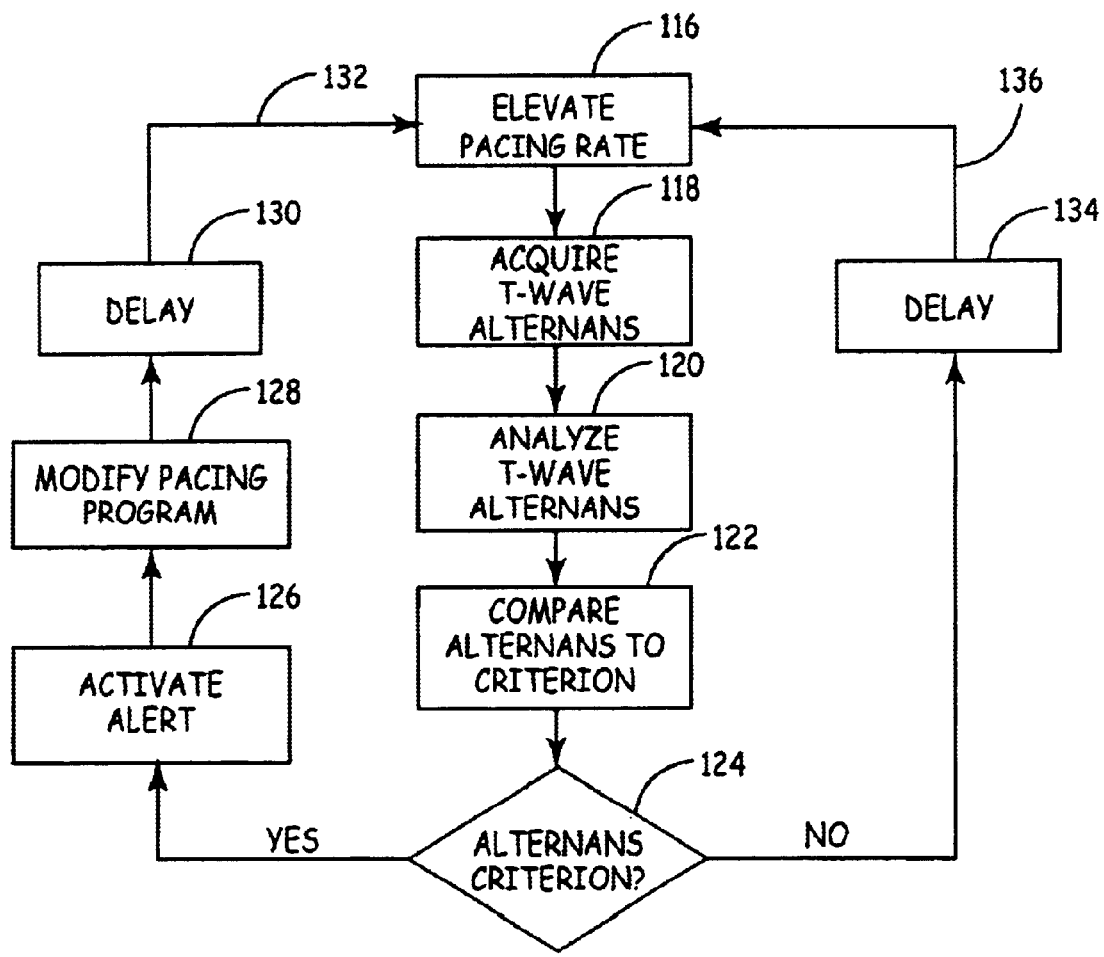
FIG. 8 is a flow diagram illustrating a method for T-wave alternans analysis in an implantable medical device in accordance with the present invention.

FIG. 8 is a flow diagram illustrating a method for T-wave alternans analysis in an implantable medical device in accordance with the present invention. The method may be performed by a system as described with reference to FIG. 7. As shown in FIG. 8, the method first involves placement of a patient in a physiological state that facilitates T-wave alternans detection. In particular, pacing controller 106 controls pacing generator 104 to elevate the pacing rate applied to the heart, as indicated by reference numeral 116. As indicated by reference numeral 118, after the heart has reached the desired pacing rate, T-wave analyzer 118 acquires the T-wave alternans data. As will be described, the T-wave alternans data can be acquired by sensing and processing a portion of the ECG signal over two or more alternating heartbeats. After acquiring the T-wave alternans data, T-wave analyzer 102 analyzes it, as indicated by reference numeral 120, using known techniques. For example, T-wave analyzer may compare one or more of a number of parameters indicative of T-wave alternans such as QT interval, T-wave amplitude, T-wave slope, T-wave power spectrum, and the like, or a combination thereof. A number of different techniques for T-wave alternans analysis are described in U.S. Pat. Nos. 5,560,368 to Berger, U.S. Pat. No. 5,560,370 to Verrier et al., U.S. Pat. No. 5,921,940 to Verrier et al., and U.S. Pat No. 5,935,082 to Albrecht et al., the entire content of each of which is incorporated herein by reference.

Once the T-wave alternans is quantified or otherwise characterized in a desired form, T-wave analyzer 102 compares it to a predetermined criterion, as indicated by reference numeral 122. In the event the alternans condition is represented as a differential average amplitude between T-waves produced for alternating heartbeats, for example, the criterion may be an amplitude threshold. As another example, the criterion could be a time difference, e.g., for alternating QT intervals. If the T-wave alternans condition is determined to satisfy or exceed the criterion, as indicated by reference numeral 124, T-wave analyzer 102 activates alert device 112, as indicated by reference numeral 126. In response, pacing controller 106 may modify the pacing program administered by pacing generator 104, as indicated by reference numeral 128, or take other therapeutic or alert-related action as described above. Following a delay, indicated by reference numeral 130, the T-wave alternans analysis may be repeated, as indicated by loop 132. Similarly, in the event significant T-wave alternans condition is not detected, the T-wave alternans analysis may be repeated following another delay, as indicated by reference numerals 134 and 136.

Figure 9A:
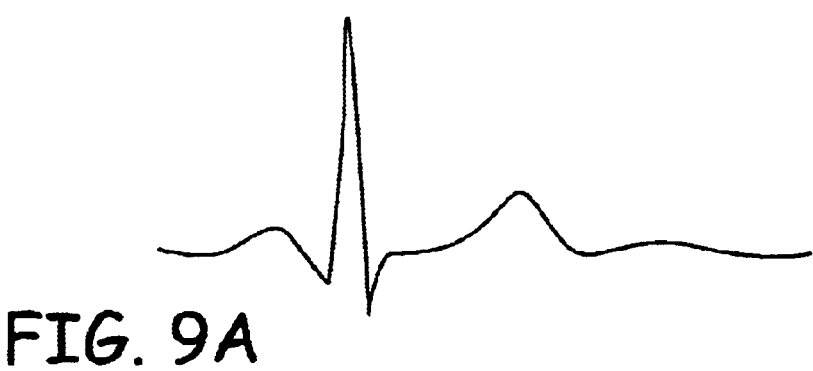
FIG. 9A illustrates an electrocardiogram signal.
Figure 9B:
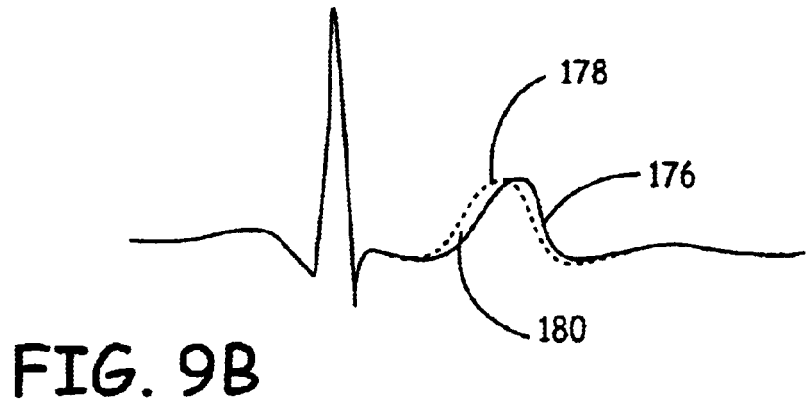
FIG. 9B illustrates a case of T-wave alternans in an electrocardiogram signal as shown in FIG. 9A.

FIG. 9A illustrates an electrocardiogram signal. FIG. 9B illustrates a simplified case of T-wave alternans in an electrocardiogram signal as shown in FIG. 9A on successive, i.e., even and odd, beats. In particular, FIG. 9B illustrates a T-wave 176 in comparison to another T-wave 178, and highlights the difference 180 between the waveforms. In most cases, the T-wave alternans is not readily visible form a simple ECG waveform. By quantifying the difference using computer-based signal analysis techniques, however, the significance of the T-wave alternans as an indicator of risk for sudden cardiac death can be determined.

Figure 10:
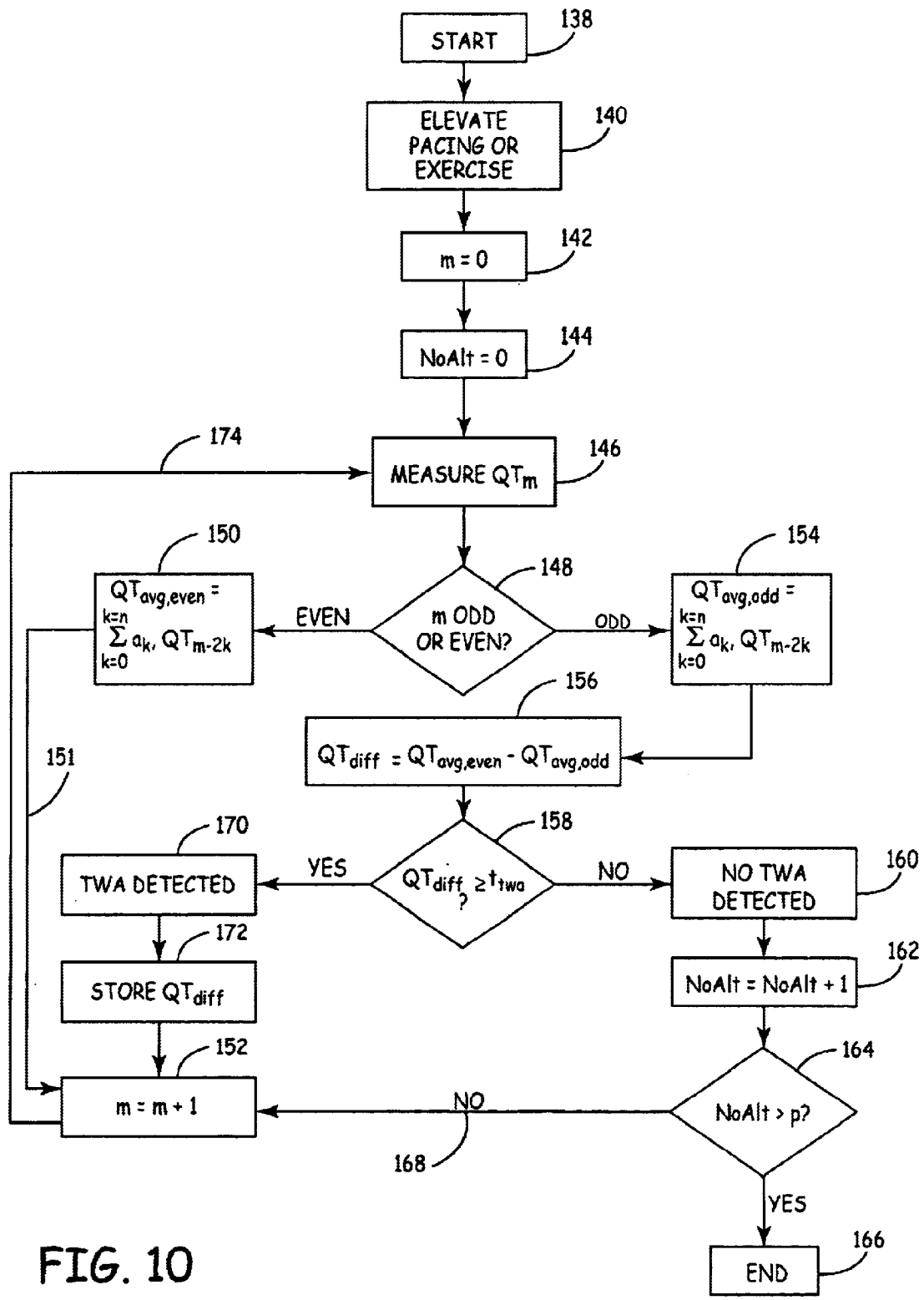
FIG. 10 is a flow diagram illustrating in greater detail a method for T-wave alternans analysis in an implantable medical device in accordance with a particular exemplary embodiment of the present invention.

FIG. 10 is a flow diagram illustrating in greater detail an exemplary method for T-wave alternans analysis. In the example of FIG. 10, the T-wave analysis focuses on differences in the QT-interval for alternating, i.e., odd and even, heartbeats in a series. At the start of the T-wave alternans analysis, indicated by reference numeral 138, the pacing stimuli is elevated to place the patient in a better condition for detection of T-wave alternans, as indicated by reference numeral 140. Alternatively, the patient engages in semi-vigorous exercise to prepare herself for the analysis. In either case, the objective is to elevate the heart rate, for example, in the range of approximately 80 to 120 beats per minute for relatively short periods of time. Once the desired physiological condition for the analysis is reached, the analysis commences by first setting two counters to zero. In particular, a counter "m," which is representative of the number of times (odd-even cycles) significant T-wave alternans is detected, is set to zero as indicated by reference numeral 142. In addition, counter "NoAlt," which is representative of the number of times (odd-even cycles) that significant T-wave alternans is not detected, is set to zero as indicated by reference numeral 144.

After setting the counters to zero, T-wave analyzer 102 measures the QT interval, as indicated by reference numeral 146. The QT interval is designated $QT_m$, with "m" identifying the sample for future reference. For example, the QT samples can be stored in memory for later analysis. The QT interval can be identified according to known signal processing techniques in the cardiology art, e.g., as described in the aformentioned U.S. Pat. Nos. 6,029,087 to Wohlgemuth. The QT interval measurement may focus on one or more different parameters useful in identifying a difference between successive QT intervals on alternating odd and even heartbeats. A number of different analysis techniques may be used such as those described in aforementioned U.S. Pat. No. 5,921,940 to Verrier et al. Known techniques for comparison of ECG morphology may include, for example, analysis of spectrum, power, amplitude, magnitude, slope, time and the like. In the example of FIG. 10, it is assumed that $QT_m$ represents the QT interval, obtained by measuring the time from QRS or stimulus until the detected T-wave.

As further shown in FIG. 10, after obtaining the $QT_m$ measurement, T-wave analyzer 102 determines whether the m counter represents an odd or even number, as indicated by reference numeral 148, and, consequently, an odd or even cycle in the alternating series of heartbeats being monitored. If m is even, T-wave analyzer 102 computes the average QT interval ($QT_{avg,even}$) based on the even-beat measurements obtained up to that time. The computation is indicated by reference numeral 150, and can be represented as follows:

$$QT_{avg,\ even} = \sum_{k=0}^{k=n} a_k QT_{m-2k} \qquad (1)$$

In the above equation, $QT_{avg,even}$ represents the average even-beat QT interval over a series of even beats from 0 to n, where n is a predetermined maximum number of odd-even cycles to be evaluated. $QT_{m-2k}$ is the measured interval for each even beat in the series, while $a_k$ is a coefficient representing weighting factors that determine the contribution of each term $QT_{m-2k}$ to the calculated average $QT_{avg,\ even}$. By choosing $a_0 = a_1 = \ldots = a_n = 1/n$, each term $QT_{m-2k}$ contributes equally to $QT_{avg,\ even}$, resulting in $QT_{avg,\ even}$ being equal to the mathematical average "even" QT interval of the last n beats. In some embodiments, by choosing $a_1 \ldots a_n$ on a non-uniform basis, emphasis may be placed on more recently measured QT intervals or any other chosen number of measured QT intervals.

After computing average even-beat QT interval, counter m is incremented by one, as indicated by reference numeral 152. Then, the process repeats by taking an odd-beat QT measurement, as indicated by loop 174 and reference numeral 146. After determining that the present QT measurement corresponds to an odd beat, based on counter m value (148), T-wave analyzer 102 computes the $QT_{avg,\ odd}$ value using an equation similar to equation (1) above, as indicated by reference numeral 154. Next, T-wave analyzer 102 computes the T-wave alternans, as indicated by reference numeral 156. The calculation of T-wave alternans is represented as:

$$QT_{diff} = |QT_{avg,\ even} - QT_{avg,\ odd}| \qquad (2)$$

The T-wave alternans measurement $QT_{diff}$ is then compared, as indicated by reference numeral 158, to a criterion in the form of an interval difference threshold $t_{twa}$ determined to be indicative of significant T-wave alternans and thus significant risk for sudden cardiac death. The value $t_{twa}$ is referred to as the T-wave alternans threshold. If the $QT_{diff}$ value does not meet or exceed $t_{twa}$ no significant T-wave alternans is detected, as indicated by reference numeral 160, and the NoAlt counter is incremented, as indicated by reference numeral 162. The NoAlt counter therefore corresponds to the number of alternating pairs, odd and even heartbeats, for which no significant T-wave alternans was detected.

If the NoAlt counter exceeds p, the predetermined maximum number of cycles to be monitored, as indicated by reference numeral 164, then the T-wave alternans analysis process ends, as indicated by reference numeral 166. In otherwords, the process stops once a predetermined number of cycles have been monitored and found to exhibit no significant T-wave alternans, suggesting that the patient is not at significant risk for sudden cardiac death. The process may be repeated, however, on a periodic basis, e.g., once a week, once a day, once every several hours, and the like. If NoAlt does not exceed the value p, the m counter is incremented as indicated by reference numeral 168 and 152, and the process is repeated to capture the next $QT_m$ even and odd and thereby calculate the next T-wave alternans value for comparison to the threshold $t_{twa}$.

If the comparison (158) indicates that $QT_{diff}$ meets or exceeds $t_{twa}$, T-wave detector 102 registers detection of a significant T-wave alternans, as indicated by reference numeral 170. The $QT_{diff}$ value is then stored in memory, as indicated by reference numeral 172, and the counter m is incremented by one, as indicated by reference numeral 152. The stored $QT_{diff}$ value may be used as the basis for activation of an alert for notification of the patient or physician or affirmative therapeutic response, as described above. In addition, the memory can be interrogated by a physician to assess the risk in greater detail. At that point, the T-wave alternans analysis process may end or repeat for the next even-odd pair as indicated by reference numeral 174. The number of times that the $QT_{diff}$ value exceeds the threshold $t_{twa}$ in the same sequence is an indicator of the duration of the alternans behavior. The absolute difference of the $QT_{even}$ intervals and the $QT_{odd}$ intervals is an indication of the magnitude of the T-wave alternans. As an alternative to calculating the different averages of odd and even QT intervals, the acute difference between $QT_{odd}$ and $QT_{even}$ can be calculated.

In any event, in accordance with the present invention, the process can be substantially confined to operations executed by the implantable device without the need for extensive physical intervention with external equipment, physician supervision, and the like. In some embodiments, it is conceivable that intermediate data obtained during the course of T-wave alternans may be conveyed to the physician or external computing devices by telemetry or otherwise. In many cases, however, activation of the alert will be sufficient following computation of T-wave alternans on a self-contained basis within the implantable medical device. The physician then many adapt therapy to the condition. Thus, with a device and method in accordance with the present invention, the physician is able to classify his patients into high risk or low risk categories. The high risk patients may need to undergo additional electrophysiologic studies, or might even directly be a proven candidate for an implantable defibrillator. Risk stratification by the use of the present invention may mean that the physician can collect proof of high risk patients without the need for documentation of a ventricular tachycardia for that specific patient, as is often required for implantation of a cardioverter/defibrillator.

FIG. 10 illustrates an embodiment in which the patient is driven into a state desirable for T-wave alternans measurement. It may be desirable, however, that T-wave analyzer 102 monitor T-wave alternans on a periodic or triggered basis including times at which the increased rate pacing stimuli has not been applied by pacing generator 104. For example, the patient may be subjected to exertion or stress in the ordinary course of his daily routine. At such times, it may be desirable to measure T-wave alternans even though the patient has not been affirmatively forced into the measurement mode, e.g., by increased rate pacing. Monitoring of stress and exertion using activity sensors and analysis of heart rate may provide a trigger for the T-wave alternans analysis. In particular, DSP 101 or equivalent analog circuitry may provide an indication of increased heart rate or other cardiac events of interest as a trigger for T-wave analyzer 102 to begin measurement of T-wave alternans. At that time, T-wave analyzer 102 may execute a routine substantially as shown in FIG. 10.

The preceding specific embodiments are illustrative of the practice of the invention. It is to be understood, therefore, that other expedients known to those skilled in the art or disclosed herein, may be employed without departing from the invention or scope of the appended claims. The present invention further includes within its scope methods of making and using the implantable medical device described above.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of wooden parts a nail and a screw are equivalent structures.

This application is intended to cover any adaptation or variation of the present invention. It is intended that this invention be limited only by the claims and equivalents thereof.

All printed publications, patent applications and patents referenced hereinabove are incorporated by reference herein, each in its respective entirety.

What is claimed is:

1. A method for analyzing cardiac electrical activity, the method comprising:

sensing electrical cardiac activity using a sensor that is implanted within the body of a patient to provide an indication of T-wave alternans within the heart of the patient;

evaluating cardiac risk based on comparison of the indication of T-wave alternans to a predetermined criterion;

sensing a state of increased heart rate by the patient, and comparing the indication of T-wave alternans to the predetermined criterion in the event the state of increased heart rate is sensed.

2. The method of claim 1, further comprising storing the T-wave alternans indication provided by the sensor in a memory associated with a device implanted within the body of the patient.

3. The device of claim 1, further comprising providing an alert in the event the indication of T-wave alternans satisfies the predetermined criterion.

4. The method of claim 1, further comprising analyzing differences in the QT interval over a series of two or more heartbeats to evaluate the cardiac risk.

5. A method for analyzing cardiac electrical activity, the method comprising:

sensing electrical cardiac activity using a sensor that is implanted within the body of a patient to provide an indication of T-wave alternans within the heart of the patient;

evaluating cardiac risk based on comparison of the indication of T-wave alternans to a predetermined criterion; and applying increased rate pacing stimuli to the heart using a pacing generator forming part of a device implanted within the body of the patient to facilitate sensing of the T-wave alternans by the sensor.

6. A method for analyzing cardiac electrical activity, the method comprising:

sensing electrical cardiac activity using a sensor that is implanted within the body of a patient to provide an indication of T-wave alternans within the heart of the patient;

evaluating cardiac risk based on comparison of the indication of T-wave alternans to a predetermined criterion based on an operation selected from a group consisting of: (i)

applying a Fourier analysis to at least a portion of the T-wave over a series of two or more heartbeats and providing the indication of T-wave alternans based on differences in the Fourier analysis over the series of two or more heartbeats; (ii) comparing alternate repolarization signals over a series of two or more heartbeats to evaluate the cardiac risk; (iii) counting the number of times the T-wave alternans satisfies the criterion, and generating an indication of cardiac risk in the event the number exceeds a predetermined threshold; (iv) analyzing a relationship between the T-wave alternans and the predetermined criterion over a period of time, and storing results of the analysis in a memory associated with a device implanted within the patient for access by a physician; (v) analyzing T-wave morphology using a digital signal processor (DSP) associated with a device implanted within the patient as a basis for the indication of the T-wave alternans.

7. The method of claim 6, further comprising applying pacing stimuli to the heart to facilitate sensing of the T-wave alternans by the sensor, and controlling the pacing stimuli based on the indication of T-wave alternans to reduce cardiac risk for the patient.

8. An implantable medical device system comprising:

a sensor that is implantable within the body of a patent to sense electrical cardiac activity and provide an indication of T-wave alternans within the heart of the patient;

a T-wave analyzer, responsive to the sensor, that evaluates cardiac risk based on comparison of the indication of T-wave alternans to a predetermined criterion; and a second sensor that senses a state of increased heart rate by the patient, wherein the T-wave analyzer is responsive to the second sensor in the evaluation of cardiac risk.

9. The system of claim 8, further comprising a pacing generator that applies increased rate pacing stimuli to the heart to facillitate sensing of the T-wave alternans by the sensor.

10. The system of claim 8, further comprising a memory that stores the T-wave alternans indication provided by the sensor.

11. The system of claim 8, further comprising a device that provides an alert in the event the indication of T-wave alternans satisfies the predetermined criterion.

12. The system of claim 8, wherein the T-wave analyzer analyzes differences in the QT interval over a series of two or more heartbeats to evaluate the cardiac risk.

13. An implantable medical device system comprising:

a sensor that is implantable within the body of a patient to sense electrical cardiac activity and provide an indication of T-wave alternans within the heart of the patient;

a T-wave analyzer, responsive to the sensor, that evaluates cardiac risk based on comparison of the indication of T-wave alternans to a predetermined criterion; and wherein the T-wave analyzer analyzes differences in the amplitude of the T-wave over a series of two or more heartbeats to evaluate the cardiac risk.

14. An implantable medical device system comprising:

a sensor that is implantable within the body of a patient to sense electrical cardiac activity and provide an indication of T-wave alternans within the heart of the patient;

a T-wave analyzer, responsive to the sensor, that evaluates cardiac risk based on comparison of the indication of T-wave alternans to a predetermined criterion; and wherein the T-wave analyzer analyzes differences in the slope of the T-wave over a series of two or more heartbeats to evaluate the cardiac risk.

15. An implantable medical device system comprising:

a sensor that is implantable within the body of a patient to sense electrical cardiac activity and provide an indication of T-wave alternans within the heart of the patient;

a T-wave analyzer, responsive to the sensor, that evaluates cardiac risk based on comparison of the indication of T-wave alternans to a predetermined criterion; and wherein the T-wave analyzer operates to perform an operation selected from a group consisting of: (i) applying a Fourier analysis to at least a portion of the T-wave over a series of two or more heartbeats and assessing cardiac risk based on differences in the Fourier analysis over the series of two or more heartbeats; (ii) comparing alternate repolarization signals over a series of two or more heartbeats to evaluate the cardiac risk; and (iii) counting the number of times the T-wave alternans satisfies the criterion and indicating cardiac risk in the event the number exceeds a predetermined threshold.

16. The system of claim 15, further comprising a memory, wherein the T-wave analyzer analyzes a relationship between the T-wave alternans and the predetermined criterion over a period of time; and stores results of the analysis in the memory for access by a physician.

17. The system of claim 15, wherein the T-wave analyzer includes a digital signal processor (DSP) that analyzes T-wave morphology as a basis for the evaluation of cardiac risk.

18. The system of claim 15, further comprising a pacing generator applies pacing stimuli to the heart to facilitate sensing of the T-wave alternans by the sensor, the system further comprising a processor that controls the pacing generator based on the indication of T-wave alternans to reduce cardiac risk for the patient.

19. An implantable cardiac pacemaker device comprising:
a pacing generator that generates electrical pacing stimuli;
one or more leads, coupled to the pacing generator, that apply the electrical pacing stimuli to the heart of a patient;
a sensor that senses electrical cardiac activity and provides an indication of T-wave alternans within the heart of the patient; and
a T-wave analyzer, responsive to the sensor, that controls the pacing generator to generate increased rate electrical pacing stimuli, whereby the desired physiological conditions for T-wave alternans analysis can be invoked to facilitate the sensing of the electrical cardiac activity by the sensor, and evaluates cardiac risk based on comparison of the indication of T-wave alternans to a predetermined criterion, wherein the T-wave analyzer analyzes differences in the amplitude of the T-wave over a series of two or more heartbeats to evaluate the cardiac risk.

20. The device of claim 19, further comprising a memory that stores the T-wave alternans indication provided by the sensor.

21. The device of claim 19, further comprising a device that provides an alert in the event the indication of T-wave alternans satisfies the predetermined criterion.

22. The device of claim 19, wherein the T-wave analyzer analyzes differences in the QT interval over a series of two or more heartbeats to evaluate the cardiac risk.

23. The device of claim 19, further comprising a pacing generator that applies pacing stimuli to the heart to facilitate sensing of the T-wave alternans by the sensor, and a controller that controls the pacing generator based on the indication of cardiac risk to reduce cardiac risk for the patient.

24. An implantable cardiac pacemaker device comprising:
a pacing generator that generates electrical pacing stimuli;
one or more leads, coupled to the pacing generator, that apply the electrical pacing stimuli to the heart of a patient;
a sensor that senses electrical cardiac activity and provides an indication of T-wave alternans within the heart of the patient; and
a T-wave analyzer, responsive to the sensor, that controls the pacing generator to generate increased rate electrical pacing stimuli, whereby the desired physiological conditions for T-wave alternans analysis can be invoked to facilitate the sensing of the electrical cardiac activity by the sensor, and evaluates cardiac risk based on comparison of the indication of T-wave alternans to a predetermined criterion, wherein the T-wave analyzer analyzes differences in the slope of the T-wave over a series of two or more heartbeats to evaluate the cardiac risk.

25. An implantable cardiac pacemaker device comprising:
a pacing generator that generates electrical pacing stimuli;
one or more leads, coupled to the pacing generator, that apply the electrical pacing stimuli to the heart of a patient;
a sensor that senses electrical cardiac activity and provides an indication of T-wave alternans within the heart of the patient; and
a T-wave analyzer, responsive to the sensor, that controls the pacing generator to generate increased rate electrical pacing stimuli, whereby the desired physiological conditions for T-wave alternans analysis can be invoked to facilitate the sensing of the electrical cardiac activity by the sensor, and evaluates cardiac risk based on comparison of the indication of T-wave alternans to a predetermined criterion, wherein the T-wave analyzer applies a Fourier analysis to at least a portion of the T-wave over a series of two or more heartbeats and evaluates cardiac risk based on differences in the Fourier analysis over the series of two or more heartbeats.

26. The device of claim 25, wherein the T-wave analyzer compares alternate repolarization signals over a series of two or more heartbeats to evaluate the cardiac risk.

27. The device of claim 25, wherein the T-wave analyzer counts the number of times the T-wave alternans satisfies the criterion, and generates an indication of cardiac risk in the event the number exceeds a predetermined threshold.

28. The device of claim 25, further comprising a memory, wherein the T-wave analyzer analyzes a relationship between the T-wave alternans and the predetermined criterion over a period of time, and stores results of the analysis in the memory for access by a physician.

29. The device of claim 25, wherein the T-wave analyzer includes a digital signal processor (DSP) that analyzes T-wave morphology as a basis for the evaluation of cardiac risk.

30. An implantable medical device system comprising:
means, implantable within the body of a patient, for sensing electrical cardiac activity and providing an indication of T-wave alternans within the heart of the patient;
means, responsive to the sensing means, for evaluating cardiac risk based on comparison of the indication of T-wave alternans to a predetermined criterion; and
means for applying increased rate pacing stimuli to the heart to facilitate sensing of the T-wave alternans by the sensing means.

31. The system of claim 30, further comprising means for sensing a state of increased heart rate by the patient, wherein the evaluating means is responsive to the state sensing means in evaluating cardiac risk.

32. The system of claim 30, further comprising means for storing the T-wave alternans indication provided by the sensing means.

33. The system of claim 30, further comprising means for providing an alert in the event the indication of T-wave alternans satisfies the predetermined criterion.

34. The system of claim 30, wherein the evaluating means analyzes differences in the QT interval over a series of two or more heartbeats to evaluate the cardiac risk.

35. The system of claim 30, wherein the evaluating means analyzes differences in the amplitude of the T-wave over a series of two or more heartbeats to evaluate the cardiac risk.

36. The system of claim 30, wherein the evaluating means analyzes differences in the slope of the T-wave over a series of two or more heartbeats to evaluate the cardiac risk.

37. The system of claim 30, wherein the evaluating means analyzes differences in T-wave characteristics over a series of two or more heartbeats to evaluate the cardiac risk.

38. The system of claim 37, wherein the evaluating means applies a Fourier analysis to at least a portion of the T-wave over a series of two or more heartbeats and provides the evaluation of cardiac risk based on differences in the Fourier analysis over the series of two or more heartbeats.

39. The system of claim 37, wherein the evaluating means compares alternate repolarization signals over a series of two or more heartbeats to evaluate the cardiac risk.

40. The system of claim 37, wherein the evaluating means counts the number of times the T-wave alternans satisfies the criterion, and generates an indication of cardiac risk in the event the number exceeds a predetermined threshold.

41. The system of claim 30, further comprising a memory, wherein the evaluating means analyzes a relationship between the T-wave alternans and the predetermined criterion over a period of time, and stores results of the analysis in the memory for access by a physician.

42. The system of claim 30, wherein the evaluating means includes a digital signal processor (DSP) that analyzes T-wave morphology as a basis for the evaluation of cardiac risk.

43. The system of claim 30, further comprising means for applying pacing stimuli to the heart to facilitate sensing of the T-wave alternans by the sensing means, the system further comprising a means for controlling the pacing generator based on the indication of T-wave alternans to reduce cardiac risk for the patient.

* * * * *